United States Patent
Bhatia et al.

(10) Patent No.: US 10,398,402 B2
(45) Date of Patent: Sep. 3, 2019

(54) METHOD AND SYSTEM FOR AUTOMATED POSITIONING OF A MEDICAL DIAGNOSTIC DEVICE

(71) Applicant: SIEMENS HEALTHCARE GMBH, Erlangen (DE)

(72) Inventors: Parmeet Singh Bhatia, Frazer, PA (US); Antony Louis Piriyakumar Douglas, Bangalore (IN)

(73) Assignee: Siemens Healthcare GmbH, Erlangen (DE)

( * ) Notice: Subject to any disclaimer, the term of this patent is extended or adjusted under 35 U.S.C. 154(b) by 40 days.

(21) Appl. No.: 15/552,759

(22) PCT Filed: Jan. 29, 2016

(86) PCT No.: PCT/EP2016/051988
§ 371 (c)(1),
(2) Date: Aug. 22, 2017

(87) PCT Pub. No.: WO2016/134916
PCT Pub. Date: Sep. 1, 2016

(65) Prior Publication Data
US 2018/0028142 A1    Feb. 1, 2018

(30) Foreign Application Priority Data
Feb. 23, 2015    (IN) .............. 197/KOL/2015

(51) Int. Cl.
*G06K 9/00*    (2006.01)
*A61B 6/00*    (2006.01)
*A61B 8/00*    (2006.01)

(52) U.S. Cl.
CPC ............ *A61B 6/547* (2013.01); *A61B 8/4263* (2013.01); *G06T 2207/10* (2013.01)

(58) Field of Classification Search
None
See application file for complete search history.

(56) References Cited

U.S. PATENT DOCUMENTS

| 5,906,578 | A | * | 5/1999 | Rajan | ................ | A61B 1/00009 600/424 |
| 7,488,108 | B2 | | 2/2009 | Pommi | | |
| 8,681,935 | B2 | | 3/2014 | Ruijters et al. | | |

(Continued)

FOREIGN PATENT DOCUMENTS

| DE | 10032982 A1 | 2/2002 |
| DE | 102007005377 A1 | 7/2008 |

(Continued)

OTHER PUBLICATIONS

PCT International Search Report and Written Opinion of the International Searching Authority dated May 3, 2016 for corresponding PCT/EP2016/051988.

*Primary Examiner* — Shervin K Nakhjavan
(74) *Attorney, Agent, or Firm* — Lempia Summerfield Katz LLC (57) ABSTRACT

A method and system are provided for automatically positioning a medical diagnostic device. The method and system use a database of images that includes reference images and user-preferred images to position the medical diagnostic device. The medical diagnostic device in an initial position is moved to a final position based on the images in the database.

15 Claims, 7 Drawing Sheets

(56) References Cited

U.S. PATENT DOCUMENTS

| | | | | |
|---|---|---|---|---|
| 2004/0034297 | A1* | 2/2004 | Darrow | A61B 34/20 |
| | | | | 600/407 |
| 2004/0076262 | A1* | 4/2004 | Shao | A61B 6/037 |
| | | | | 378/196 |
| 2004/0097805 | A1* | 5/2004 | Verard | A61B 1/00071 |
| | | | | 600/428 |
| 2007/0030957 | A1 | 2/2007 | Pommi | |
| 2008/0119725 | A1* | 5/2008 | Lloyd | A61B 90/36 |
| | | | | 600/424 |
| 2010/0067739 | A1 | 3/2010 | Mostafavi et al. | |
| 2011/0160570 | A1* | 6/2011 | Kariv | A61B 5/721 |
| | | | | 600/424 |
| 2014/0161337 | A1* | 6/2014 | Raykar | G06K 9/6202 |
| | | | | 382/131 |

FOREIGN PATENT DOCUMENTS

| | | |
|---|---|---|
| DE | 20321723 U1 | 3/2009 |
| DE | 102009058509 A1 | 6/2011 |
| DE | 102012205238 A1 | 10/2013 |
| DE | 102011006574 B4 | 11/2014 |
| WO | WO2013144912 A1 | 10/2013 |

* cited by examiner

METHOD AND SYSTEM FOR AUTOMATED POSITIONING OF A MEDICAL DIAGNOSTIC DEVICE

CROSS REFERENCE TO RELATED APPLICATIONS

This present patent document is a § 371 nationalization of PCT Application Serial Number PCT/EP2016/051988, filed Jan. 29, 2016, designating the United States, which is hereby incorporated in its entirety by reference. This patent document also claims the benefit of 197/KOL/2015, filed on Feb. 23, 2015 which is also hereby incorporated in its entirety by reference.

FIELD

Embodiments relate to a method and system for automated positioning of a medical diagnostic device based on one or more images from a database.

BACKGROUND

Alignment of medical diagnostic device during intervention or surgery is a time consuming process. A physician requires experience to reduce radiation exposure time for a patient. In the current diagnostic devices allow a user to align the diagnostic device manually. Moving the medical diagnostic device manually to arrive at an optimal position is cumbersome and requires experience.

SUMMARY

The scope of the present invention is defined solely by the appended claims and is not affected to any degree by the statements within this summary. The present embodiments may obviate one or more of the drawbacks or limitations in the related art. Embodiments provide for automatically moving a medical diagnostic device to a desired position allowing a user to save time and effort in manually adjusting the position of the medical diagnostic device.

A method for positioning a medical diagnostic device is provided. The method includes determining, by a processor, a current position of a medical diagnostic device (e.g. medical imaging device) by comparing a current image with at least one reference image in a first database. The first database may be a database of reference images. The reference images may include images of a subject at various positions of the medical diagnostic device. Further, the method includes determining a target position coordinates by comparing the current image with at least one preferred image in a second database and computing a similarity score. The second database is a database of user preferred images to which the diagnostic device needs to be repositioned. The similarity score is computed based on the similarity in the features of the images as well as the position coordinates. The similarity score is a measure of the closeness of the medical diagnostic device to the target position. Further, motion parameters of a target position coordinates of the medical diagnostic device are computed iteratively, based on the similarity score. The motion parameters are calculated based on the position coordinates of the images from at least one of the first and the second database. The motion parameters are generated such that the medical diagnostic device eventually reaches the target position. Finally, a movement of the medical diagnostic device is actuated to arrive at the target position based on the motion parameters. The target position may be a view of the subject's anatomy as recorded in the user preferred image.

In an embodiment, the similarity score is based on the similarity between the features of the first image and the at least one reference image. Further, the similarity score may also depend upon position coordinates associated with the first image and the reference image.

In another embodiment, one or more intermediate position coordinates are computed, resulting in one or more intermediate positions, if the similarity score is below a threshold value. When the similarity score is above a threshold value, the medical diagnostic device will have reached the target position.

In another embodiment, the first image is updated when the imaging device is in the one or more intermediate positions. The medical diagnostic device captures a new image at every intermediate position and compares the new image with a reference image to track the movement of the medical diagnostic device towards the target position.

In another embodiment, the second database includes one or more user preferred images generated during a manual operation of the medical diagnostic device. The user preferred images may be obtained by the user during the manual operation of the medical diagnostic device. The user may desire the same view to be repeated by automatic positioning.

In another embodiment, machine learning models are used for receiving feedback position coordinates in case the target position is changed manually. When the user manually adjusts the position of the medical diagnostic device the position coordinates, the feedback is recorded and analyzed to make adjustment automatically next time a similar target position is desired.

In another embodiment, personalized position coordinates and motion parameters are generated for different users based on machine learning models. The user profile may be stored and the most common target positions may be automatically retrieved based on the user profile.

In an embodiment, the images in the first and second databases include position coordinates as meta information. The position coordinates translate the region of the anatomy in the image to a position of the medical diagnostic device.

In an embodiment, a system for performing positioning of the medical diagnostic device is provided to reduce the time and effort for positioning the medical diagnostic device. The system includes a processor and a memory coupled with the processor. The memory includes processor executable instructions in the form of position guidance module for determining a current position of the medical diagnostic device by comparing a current image with at least one reference image in a first database. The position guidance module is configured for determining a target position coordinates by comparing the current image with at least one preferred image in a second database and computing a similarity score. Thereafter, the position guidance module is configured to compute motion parameters of a target position coordinates of the medical diagnostic device iteratively, based on the similarity score. The position guidance module is configured to compute the position coordinates of the medical diagnostic device iteratively. At every iteration, the medical diagnostic device is positioned closer to the target position. Further, the position guidance module is configured to actuate movement of the medical diagnostic device to the target position based on the motion parameters. For example, the position guidance module the motion coordinates may be electrical signals that actuate one or more motors of the medical diagnostic device to move in a direction.

In an embodiment, the position guidance module is configured to compute the similarity score based on the similarity between at least one of the current image and the preferred image, and the motion coordinates associated with the current image and the preferred image.

In another embodiment, the position guidance module is configured to use machine learning models to incorporate feedback based on a change in target position. The change in the position from the target position, that the user performs manually, is analyzed and the target position coordinates may be updated to the new target position based on the manual fine tuning of the user.

In another embodiment, the position guidance module is configured to compute one or more intermediate position coordinates and intermediate motion parameters based on the similarity score. The position guidance is an iterative process where the motion coordinates are calculated based on the similarity between a current image and a preferred image. The position guidance module is configured to generate a similarity score based on the similarity between the current image and a preferred or target image. When the similarity score exceeds a threshold value then the target position of the medical diagnostic device is met.

In another embodiment, the position guidance module is configured to generate personalized position coordinates and motion parameters for different users based on machine learning models. The machine learning models may be employed to learn the positioning requirements of different users and automatically position the medical diagnostic device to the requirement when a particular user profile is invoked. In another embodiment, the medical diagnostic device is a medical imaging device or a patient care device.

DETAILED DESCRIPTION

Various embodiments are described with reference to the drawings, where like reference numerals are used to refer to like elements throughout. In the following description, for the purpose of explanation, numerous specific details are set forth in order to provide thorough understanding of one or more embodiments. Such embodiments may be practiced without these specific details.

Figure 1:
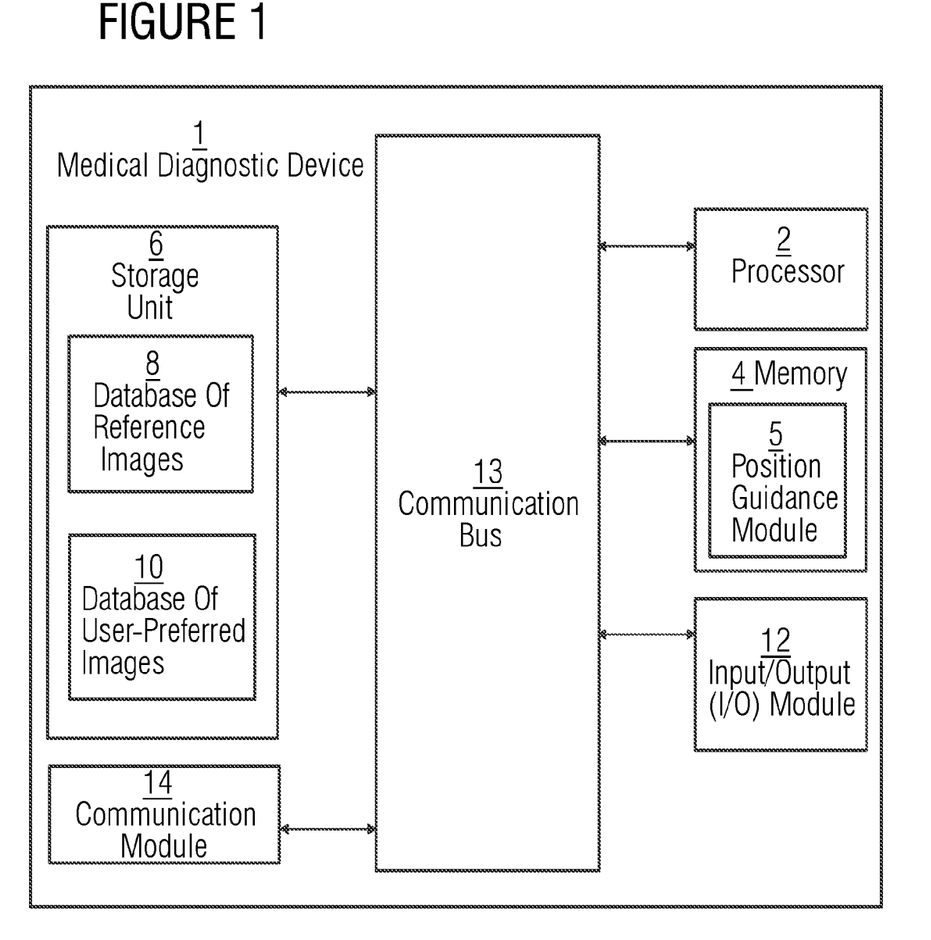
FIG. 1 illustrates a device for positioning a medical diagnostic device according to an embodiment.

FIG. 1 illustrates an exemplary device 1 for positioning a medical diagnostic device, in accordance with an embodiment. The device 1 includes a processor 2, a memory 4, a storage unit 6, an Input/Output (I/O) module 12, and a communication module 14. The components of the device 1 are communicatively coupled using a communication bus 13. Further, the storage unit 6 may include image databases 8 and 10 that include one or more images used in positioning the medical diagnostic device.

The processor 2 may be any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processor 2 may also include embedded controllers, such as generic or programmable logic devices or arrays, application specific integrated circuits, single-chip computers, and the like.

The memory 4 may be volatile memory and non-volatile memory. The memory 4 may be coupled for communication with the processor 4. The processor 2 may execute instructions and/or code stored in the memory 4. A variety of computer-readable storage media may be stored in and accessed from the memory 4. The memory 4 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory includes a position guidance module 5 that is stored in the form of machine-readable instructions on any of the above-mentioned storage media and may be in communication with and executed by the processor 2. The position guidance module 5 further includes modules that, when executed by the processor 2, result in the automatic positioning of the medical diagnostic device based on one or more images in the database. The functionalities of the modules are described in greater detail in conjunction with FIG. 2.

The storage unit 8 may be a non-transitory storage medium that stores the images. In an embodiment, the storage unit 8 may store image databases. The storage unit 8 may include a database of reference images 8 and a database of user preferred images 10. The images from the databases 8 and 10 are used for positioning the medical diagnostic device. The communication interface 14 allows the device 1 to communicate with other connected devices via wired or wireless communication protocol known in the art. The input/output unit 12 may include inputs such as a keypad, a touch sensitive display configured to receive input signal, and outputs such as a speaker, a printer, or a display for outputting, for example, the model of the vessel stent. The communication bus 14 provides an interconnect between the processor 4, the memory 6, the storage unit 8, the communication interface 7, and the input/output unit 10.

Figure 2:
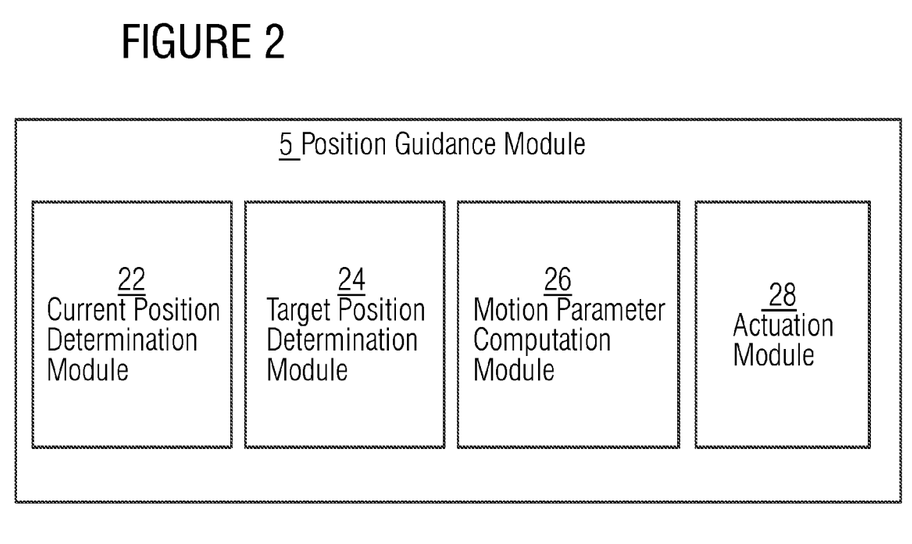
FIG. 2 illustrates a block diagram of position guidance module according to an embodiment.

FIG. 2 illustrates an exemplary block diagram of position guidance module 5, in accordance with an embodiment. The position guidance module 5 is configured to position the medical diagnostic device to a target position based on reference images and user preferred images. The medical diagnostic device may include, for example, an imaging modality or a patient care device. The position guidance module 5 includes a current position determination module 22, a target position determination module 24, a motion parameter computation module 26, and an actuation module 28. In an embodiment, the current position determination module 22 is configured to determine a current position of the medical diagnostic device based on a current image. The current image may be an image capturing the current position of the medical diagnostic device. For example, the resting position of the medical diagnostic device may be facing a facial region of a patient. The current image may capture a facial region of the subject. The current image is compared with one or more reference images to determine the current position of the medical diagnostic device. The database of reference images 8 is created by storing images captured by the medical diagnostic device with possible positions with respect to a patient. The database of reference images 8 may be manually created. Further, the target position determination module 24 is configured to determine a target position of the medical diagnostic device as preferred by a user. In order to determine the target position, the database of user preferred images 10 is used. The database of user preferred images 10 may include one or more images of desired views of users using the medical diagnostic device. The images in the database 8 and database 10 may include position coordinates as meta information. The position coordinates may be used to determine the path of the medical diagnostic device. The target position is determined based on the user and the corresponding view the user is desired to have. The target position of the medical diagnostic device may be manually adjusting the position of the medical diagnostic device and generating a target image. For example, a user may require a target position of the medical diagnostic device facing the lung region of the patient. In such a case, the user may manually adjust the medical diagnostic device to the desired lung region and capture the image. The image is then stored in the database of user preferred images 10, that may be accessed by the target position determination module 26. The target position determination module 26 computes the target position coordinates based on the comparison between the current image and the target image. Further, the target position determination module 26 computes a similarity score between the current image and the user preferred image. The similarity score may be based on the features of the images or the motion coordinates associated with the images. For example, if the current position of the medical diagnostic device is facing the leg portion of the patient and the user preferred position is the head portion of the patient, then the similarity score will be smaller or lower and position coordinates are calculated to move the medical diagnostic device towards the head portion of the patient. Similar computation may be performed based on the position coordinates associated with the current image and the user preferred image. In another example, the target position coordinates are computed iteratively while traversing towards the target position. For example, the medical diagnostic device facing a leg portion of the patient may iteratively compare the images while traversing from the leg portion to the head portion in order to confirm that the medical diagnostic device is traversing in the right path.

Upon determining the target position coordinates, motion parameters associated with the target position coordinates are computed by the motion parameter computation module 26. The motion control of the medical diagnostic device may be performed by a Programmable Logic Controller (PLC) (not shown). The motion parameters may be computed for other motion control mechanisms. The motion parameters may include signals to the motors of the medical diagnostic device to change the position of the medical diagnostic device closer to the target position. For example, the target position coordinates may indicate that the medical diagnostic device is to be moved towards the right from the current position. The motion parameter computation module 26 determines the values to be provided to the PLC so that the medical diagnostic device moves closer to the desired target position. The actuating module 28 is configured to move the medical diagnostic device towards the target position. The actuating module 28 may control the mechanical parts of the medical diagnostic device that provide the movement thereof.

During the traversal of the medical diagnostic device from the current position to the target position, there may be one or more intermediate positions. For example, when the medical diagnostic device traverses from the leg portion of the patient towards the head portion, there may be intermediate positions taken by the medical diagnostic device. The target position determination module 26 iteratively checks the current position and the target position to realign the movement of the medical diagnostic device. The deviation of the medical diagnostic device from the target position is determined by the similarity score. For example, the similarity score may range from 0 to 1, where 0 indicates that the position is heavily deviating from the target position and 1 indicates that the target position is achieved. Accordingly, a threshold value may be set in the target position determination module to indicate if the target position is to be recalculated. In an embodiment, the threshold value of the similarity score is set at 0.95. Further, one or more machine learning models may be implemented in the target position determination module 26. The machine learning models implemented in the target position determination module 26 may include, for example, Support Vector Machine (SVM), Bayesian Models, deep neural networks, random forests and the like. The machine learning models enable the target position determination module 26 to learn from the deviations made by the medical diagnostic device and gradually reduce the deviations. The machine learning models may be trained using reference images and user preferred images to increase the accuracy and reliability.

In an embodiment, the machine learning models may be used to provide motion guidance to the medical diagnostic device based on user profiles. The position guidance module 5 may include a way (e.g., a device) to create user profiles and submit user preferred images separately. The machine learning models implemented in the position guidance module 5 learn the frequently used positions of the users and suggest the target positions based on the user profile without requiring new user preferred images. Further, the machine learning models may analyze the manual changes performed after reaching a target position and fine tune the target position of the medical diagnostic device.

Figure 3:
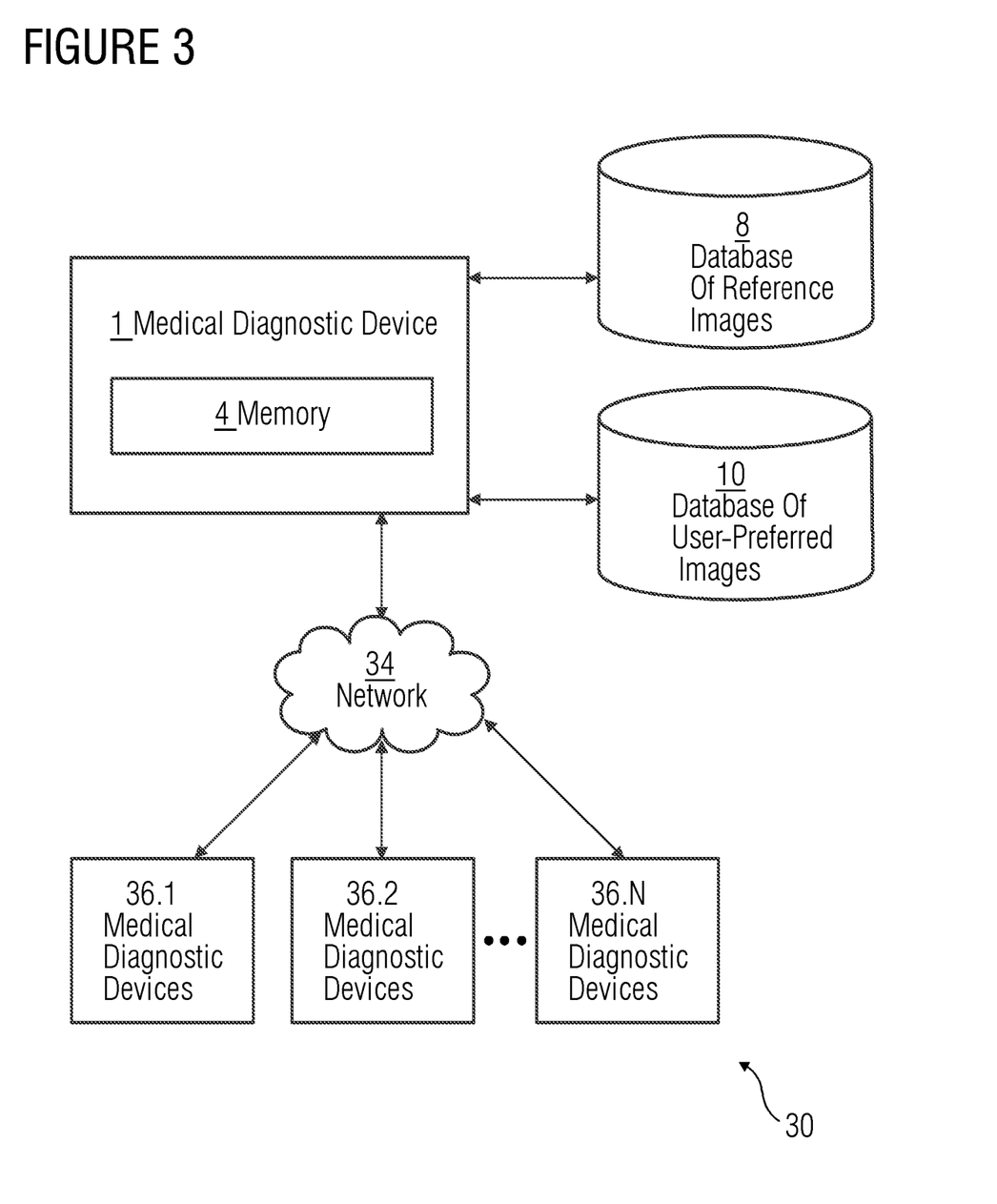
FIG. 3 illustrates a system for positioning the diagnostic medical device according to an embodiment.

FIG. 3 illustrates an exemplary system 30 for positioning the diagnostic medical device, in accordance with an embodiment. The system 30 includes the device 1 as a central server. The device 1 has access to the database of reference images 8 and database of user preferred images. The device 1 is communicatively coupled with one or more medical diagnostic devices 36.1-36.N through a network 34. The network 34 may be any of known wired or wireless networks. The medical diagnostic devices may include imaging modalities such as MRI scanning devices, Ultrasound scanning devices, X-ray based devices and PET scanning devices. The motion of the medical diagnostic device may be performed by an electromechanical system that includes, for example, programmable logic controllers (PLCs), stepper motor drives, and other similar devices. The medical diagnostic devices may include patient care devices such as a ventilator. The device 1 accesses the database 8 and database 10 for providing motion guidance to the medical diagnostic devices 36.1-36.N. The images in the database 8 and the database 10 may be segregated based on the type of the medical diagnostic devices 36.1-36.N. Further, the images in the database 8 and the database 10 may be grouped based on the user profiles. The position guidance module 5 stored in the device 1 may position the medical diagnostic devices 36.1-36.N, as described above with reference to FIG. 2.

Figure 4:
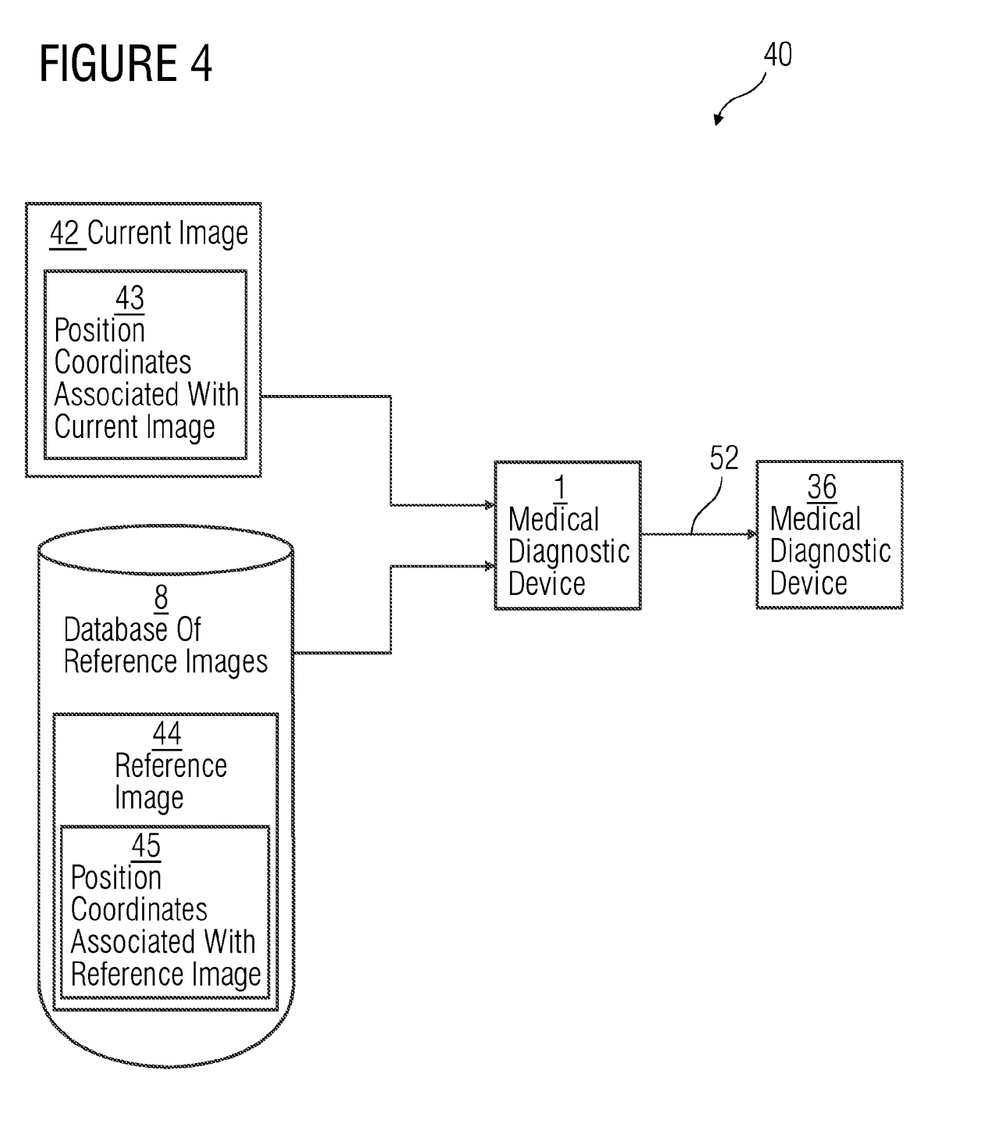
FIG. 4 illustrates a block diagram of positioning the medical diagnostic device based on reference images according to an embodiment.

FIG. 4 illustrates an exemplary block diagram 40 of positioning the medical diagnostic device 36 based on reference images, in accordance with an embodiment. In FIG. 4, a current image 42, with corresponding position coordinates as meta information, is received by the device 1. The device 1 may receive the current image 42 from a medical diagnostic device. Further, the device 1 accesses the database of reference images 8 to determine the matching reference image 44. The matching reference image includes the associated position coordinates 45 as meta information. Using the matching reference image, the current position coordinates of the medical diagnostic 36 is determined. In an example, the current image 42 capture by the medical diagnostic device 36 may include a leg portion of the patient. The database of reference images 8 is searched for a substantially matching image 44. The similarity score is computed, and the position coordinates are determined based on the matching reference image 44.

Figure 5:
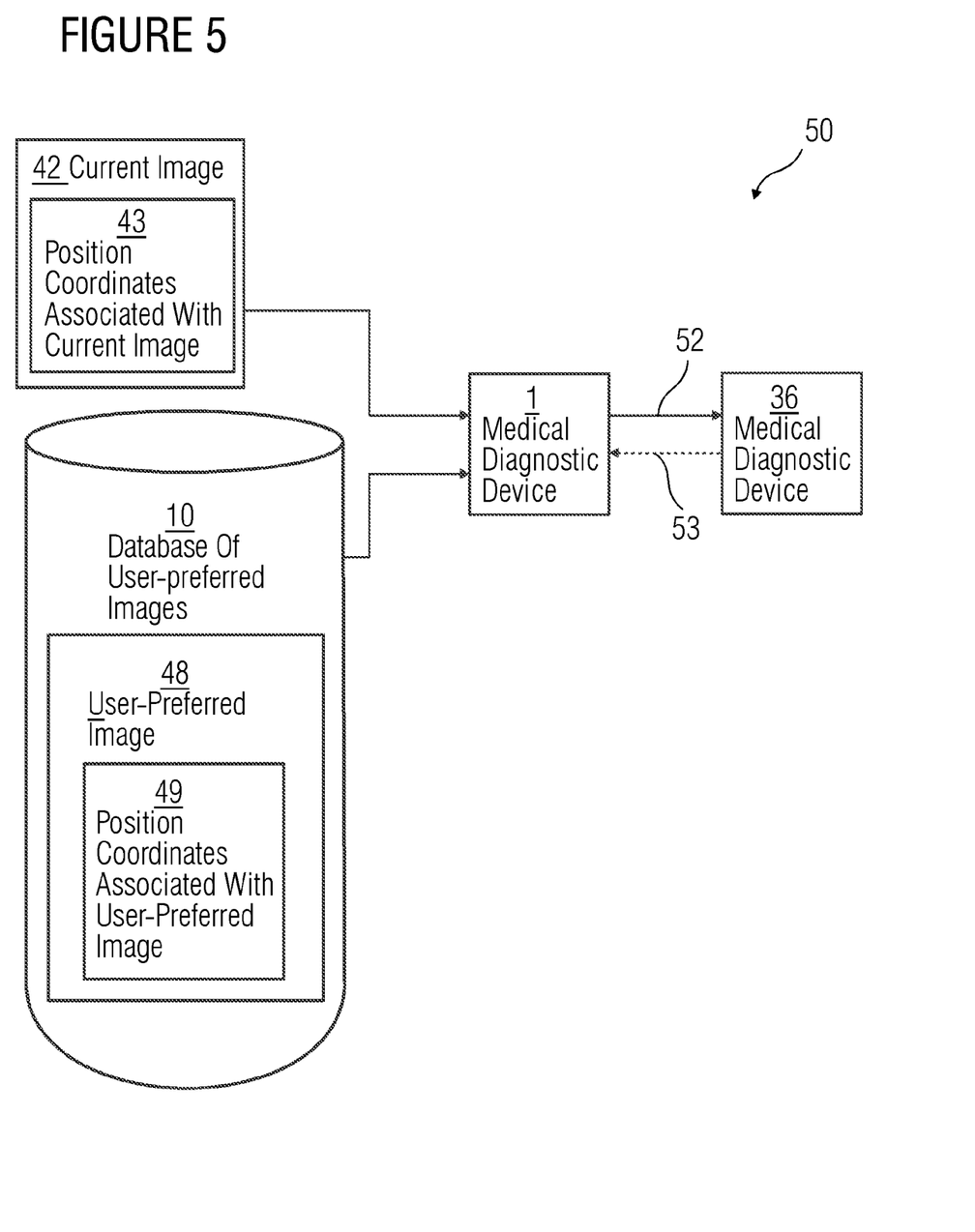
FIG. 5 illustrates a block diagram of positioning the medical diagnostic device based on user preferred images according to an embodiment.

FIG. 5 illustrates an exemplary block diagram of positioning the medical diagnostic device based on user-preferred images, in accordance with an embodiment. Upon determining the current position of the medical diagnostic device 36, the database of user-preferred images 10 is accessed, by device 1, to determine the target position of the medical diagnostic device. The device 1 retrieves a user preferred image 48 having associated position coordinates 49. The device 1 compares the current image 42 with the user preferred image 48 and computes a similarity score. Based on the similarity score, the device 1 communicates motion parameters 52 to the medical diagnostic device 30. The medical diagnostic device 36 is moved, based on the motion parameters 52, to match with the user preferred image 48. The movement of the medical diagnostic device 36 may be performed iteratively referring to the reference images and user preferred images to guide the motion of the medical diagnostic device 36. If any manual adjustments in the target position are performed by the user, the adjustments are provided to the device 1 as feedback signal 53. The feedback signal 53 is analyzed by the machine learning models to fine tune the target position during subsequent positioning of the medical diagnostic device 36.

Figure 6:
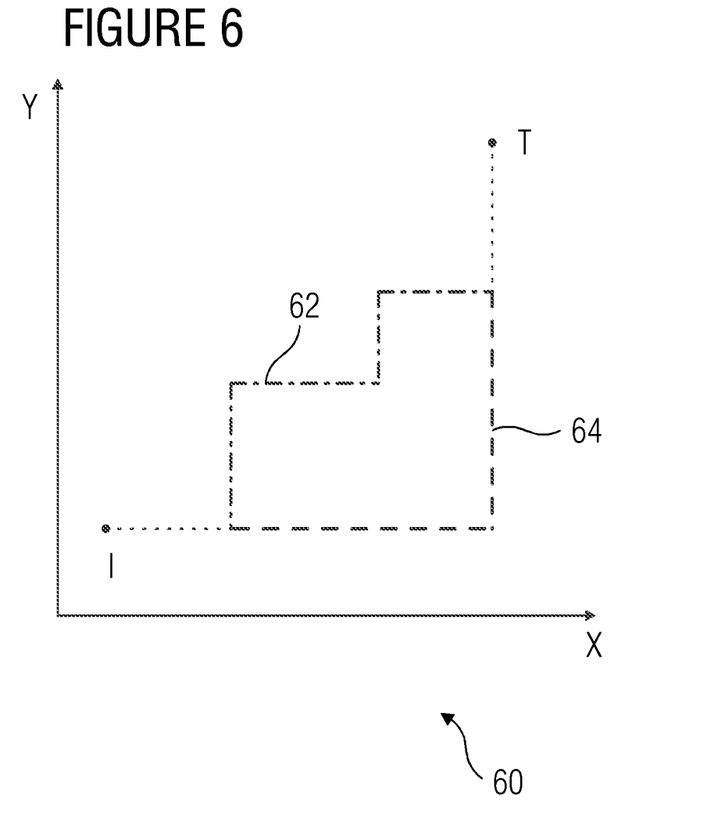
FIG. 6 illustrates a path traversed the medical diagnostic device according to an embodiment.

FIG. 6 illustrates a schematic 60 of one or more exemplary paths (62, 64) traversed by the medical diagnostic device, in accordance with an embodiment. The device 1 may cause the medical diagnostic device 36 to traverse a path while positioning the medical diagnostic device to a target position. In FIG. 6, an initial position is defined as I and the target position is defined as T. The device 1 may guide the medical diagnostic device from I to T through paths such as 62 and 64. Path 62 is more laborious than path 64. Initially, the device 1 may guide the medical diagnostic device along path 62. The machine learning models of the position guidance module 5, over many such traversals, learns that the path 64 is easier and hence adopts the path 64 for subsequent traversals. The path 64 may be set as a favorite for a particular user who requires the target position T more often. FIG. 6 illustrates an exemplary two dimensional case, whereas the motion of the medical diagnostic device is in the three dimensional space and may be extended to six dimensions when orientation parameters are considered.

Figure 7:
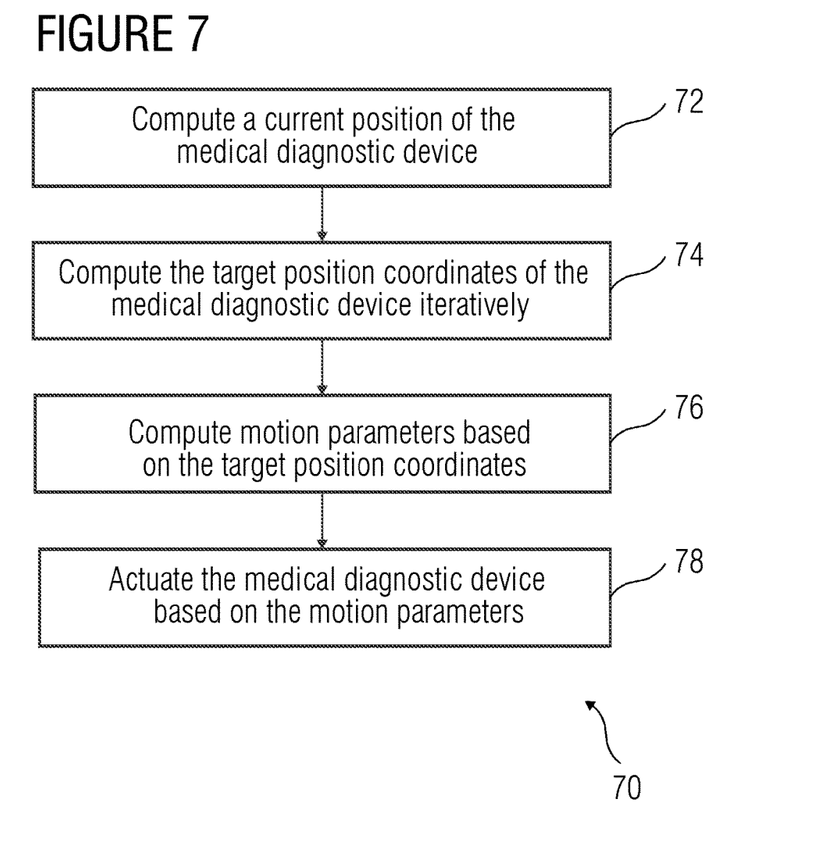
FIG. 7 illustrates a block diagram for positioning the medical diagnostic device according to an embodiment.

FIG. 7 illustrates an exemplary block diagram 70 of method acts involved in positioning the medical diagnostic device, in accordance with an embodiment. At act 72, a current position of the medical imaging device is determined by comparing a current image with at least one reference image in a first database. At act 74, target position coordinates and a similarity score are determined, iteratively, by comparing the current image with at least one of the reference image and a user preferred image in a second database (e.g., the reference image and/or the user preferred image). The target position coordinates are determined iteratively by traversing along a path based on the similarity score. The similarity score is a measure of the closeness of the current position with the target position. There may be one or more intermediate positions of the medical diagnostic device before arriving at the target position. Further, one or more machine learning models may be employed to learn the target positioning and fine tuning. In an example, the machine learning algorithms are configured to learn motion parameters and cause the medical diagnostic device to move from one position to the next in optimal steps. Further, machine learning models may be used to provide personalized target positioning based on user profiles. At act 76, motion parameters associated with the target position coordinates of the medical diagnostic device are computed. The motion parameters are the signals provided to the PLC units (not shown) of the medical diagnostic devices in order to actuate movement. Based on the target position coordinates, the motion parameters may vary. At act 78, movement of the medical diagnostic device to the target position is actuated based on the motion parameters. The mechanical components responsible for the motion of the medical diagnostic device are actuated.

The method and system disclosed herein reduces exposure of patients to radiation dosage during alignment of the medical diagnostic device. The target position is reached by taking a minimum number of images. The method eliminates the time and energy expended by physicians in manually adjusting the view of the medical diagnostic device. The best view or position is attained in less time. Further, maintaining individual profiles of views coupled with machine learning models provides personalized target view positioning. The method and system minimizes the time required for interventions by positioning the medical device in a short time interval.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

We claim:

1. A method for positioning a medical diagnostic device, the method comprising:
    determining, by a processor, a current position of the medical diagnostic device, the determining of the current position of the medical diagnostic device comprising comparing a current image with at least one reference image in a first database;
    determining, by the processor, target position coordinates and a similarity score iteratively, the determining of the target position coordinates and the similarity score comprising: comparing the current image with the at least one reference image, a user preferred image in a second database, or the at least one reference image and the user preferred image; and computing one or more intermediate position coordinates for one or more intermediate positions when the similarity score is below a threshold value, wherein the current image is updated when the medical diagnostic device is in the one or more intermediate positions;
    computing, by the processor, one or more motion parameters associated with the target position coordinates of the medical diagnostic device;
    actuating, by the processor, movement of the medical diagnostic device to a target position based on the one or more motion parameters.

2. The method of claim 1, wherein the similarity score is based on a similarity between the current image and the at least one reference image and position coordinates associated with the current image, and the at least one reference image.

3. The method of claim 1, wherein the second database comprises one or more reference images generated during a manual operation of the medical diagnostic device.

4. The method of claim 1, further comprising identifying, using a machine learning model, feedback position coordinates when the target position is changed manually.

5. The method of claim 1, further comprising generating personalized position coordinates and motion parameters for different users based on one or more machine learning models.

6. The method of claim 1, wherein the at least one reference image in the first database and the user preferred image in the second database include position coordinates as meta information.

7. The method of claim 1, wherein the medical diagnostic device is a medical imaging device.

8. The method of claim 1, wherein the medical diagnostic device is a patient care device.

9. A system for positioning a medical diagnostic device, the system comprising:
    a processor; and
    a memory coupled with the processor, wherein the memory includes processor executable instructions in the form of a position guidance module to:
        determine a current position of the medical diagnostic device, the determination of the current position of the medical diagnostic device comprising comparison of a current image with at least one reference image in a first database;
        calculate a similarity score for the current image;
        determine target position coordinates, the determination of the target position coordinates comprising: computation of one or more intermediate position coordinates for one or more intermediate positions when the similarity score is below a threshold value, wherein the current image is updated when the medical diagnostic device is in the one or more intermediate positions and comparison of the current image with at least one preferred image in a second database;
        calculate one or more motion parameters of the target position coordinates of the medical diagnostic device iteratively, based on the similarity score; and
        actuate movement of the medical diagnostic device to a target position based on the one or more motion parameters.

10. The system of claim 9, wherein the position guidance module is configured to calculate the similarity score based on a similarity between the current image, the at least one preferred image, or the current image and the at least one preferred image and motion coordinates associated with the current image and the at least one preferred image.

11. The system of claim 9, wherein the position guidance module is further configured to use machine learning models to incorporate feedback based on a change in the target position.

12. The system of claim 9, wherein the position guidance module is further configured to calculate the one or more intermediate position coordinates and one or more intermediate motion parameters based on the similarity score.

13. The system of claim 9, wherein the position guidance module is further configured to generate personalized position coordinates and personalized motion parameters for different users based on one or more machine learning models.

14. The system of claim 9, wherein the medical diagnostic device is a medical imaging device.

15. The system of claim 9, wherein the medical diagnostic device is a patient care device.

* * * * *